United States Patent
Ni

(10) Patent No.: US 8,759,429 B2
(45) Date of Patent: Jun. 24, 2014

(54) FLAME-RETARDANT COPOLYETHERESTER COMPOSITION AND ARTICLES COMPRISING THE SAME

(71) Applicant: E I Du Pont De Nemours and Company, Wilmington (DE)

(72) Inventor: Yong Ni, Shanghai (CN)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/706,442

(22) Filed: Dec. 6, 2012

(65) Prior Publication Data

US 2013/0146330 A1    Jun. 13, 2013

(30) Foreign Application Priority Data

Dec. 7, 2011    (CN) .......................... 2011 1 0404591

(51) Int. Cl.
*C08K 5/5313*    (2006.01)

(52) U.S. Cl.
USPC ............. 524/126; 524/99; 524/100; 524/127; 524/133; 524/140; 524/141

(58) Field of Classification Search
USPC ............ 524/99, 100, 126, 127, 133, 140, 141
See application file for complete search history.

(56) References Cited

U.S. PATENT DOCUMENTS

| | | | |
|---|---|---|---|
| 6,136,973 A | 10/2000 | Suzuki et al. | |
| 6,169,131 B1 * | 1/2001 | Goertz et al. | ................. 524/101 |
| 2005/0101706 A1 | 5/2005 | Bauer et al. | |
| 2011/0071240 A1 | 3/2011 | Ding et al. | |

FOREIGN PATENT DOCUMENTS

| | | | |
|---|---|---|---|
| EP | 1 430 097 | * | 6/2004 |
| EP | 1466946 A1 | | 10/2004 |
| EP | 1389226 B1 | | 5/2006 |
| EP | 1 883 081 | * | 1/2008 |
| EP | 2322577 A1 | | 5/2011 |
| KR | 10 1190971 | * | 10/2012 |
| KR | 2010 0038701 | * | 10/2012 |
| WO | WO 96/16948 | * | 11/1995 |
| WO | WO 98/39306 | * | 9/1998 |
| WO | WO 2004/014993 | * | 2/2004 |
| WO | WO 2007/010318 | * | 1/2007 |
| WO | WO 2008/011939 | * | 1/2008 |
| WO | WO 2008/060549 | * | 5/2008 |
| WO | WO 2009/047353 | * | 4/2009 |
| WO | WO 2010/094560 | * | 8/2010 |
| WO | WO 2011/072459 | * | 6/2011 |
| WO | WO 2011/120225 | * | 10/2011 |

* cited by examiner

*Primary Examiner* — Peter Szekely

(57) ABSTRACT

Disclosed herein is a flame-retardant copolyetherester composition comprising: (a) at least one copolyetherester; (b) about 5-35 wt % of at least one halogen-free flame retardant; (c) about 0.1-20 wt % of at least one nitrogen-containing compound; (d) about 0.1-10 wt % of at least one aromatic phosphate and (e) about 0.1-10 wt % of at least at least one novolac resin. Further disclosed herein are articles comprising component parts formed of the flame-retardant copolyetherester composition.

20 Claims, No Drawings

FLAME-RETARDANT COPOLYETHERESTER COMPOSITION AND ARTICLES COMPRISING THE SAME

CROSS REFERENCE TO RELATED APPLICATIONS

This application claims the benefit of Chinese Patent Application No. 20111040459.5, filed Dec. 7, 2011, now pending, the entire disclosure of which is incorporated herein by reference.

TECHNICAL FIELD

The disclosure is related to flame-retardant copolyetherester compositions and articles comprising the same.

BACKGROUND

Due to its excellent mechanical properties (e.g., tear strength, tensile strength, flex life, and abrasion resistance), polymeric compositions based on copolyetherester elastomers have been used in forming components for motorized vehicles and electrical/electronic devices. However, often times, electric arc may be formed and high temperature may be reached within the under-hood areas of vehicles and inside electrical/electronic devices. Thus, while maintaining other mechanical properties, it is desirable that such copolyetherester based compositions also have low flammability and high thermal stability.

Various flame retardant systems have been developed and used in polymeric material, e.g., polyesters, to improve the flame-retardancy thereof. However, due to toxicity concerns, halogen-free flame retardants are gaining more and more attention. Among the various halogen-free flame retardants, phosphorus compounds (such as salts of phosphinic or diphosphinic acids) are used the most due to the stability and flame retardant effectiveness thereof. Prior art has also demonstrated that various types of synergistic compounds can be used as synergists in combination with the phosphorus compounds to further maximize the flame retardant effectiveness thereof. For example, U.S. Pat. No. 6,547,992 discloses the use of synthetic inorganic compounds such as oxygen compounds of silicon, magnesium compounds, metal carbonates of metals of the second main group of the periodic table, red phosphorus, zinc compounds, aluminum compounds, or combinations thereof as flame retardant synergists; U.S. Pat. No. 6,716,899 discloses the use of organic phosphorus-containing compounds as flame retardant synergists; U.S. Pat. No. 6,365,071 discloses the use of nitrogen-containing compounds (e.g., melamine cyanurate, melamine phosphate, melamine pyrophosphate, or melamine diborate) as flame retardant synergists; and U.S. Pat. No. 6,255,371 discloses the use of reaction products of phosphoric acids with melamine or condensed product of melamine (e.g., melamine polyphosphate (MPP)) as flame retardant synergists.

Particularly, European Patent Publication No. EP1883081 and PCT Patent Publication Nos. WO2009/047353 and WO2010/094560 each discloses flame retardant elastomeric compositions useful in forming the insulating layers and/or jackets of wires and cables. In those disclosures, combinations of (i) a metal salt of a phosphinic acid and/or a diphosphinic acid, (ii) a nitrogen containing compound (e.g., melamine polyphosphate), and (iii) an inorganic compound (e.g., zinc borate) are taught as preferred flame retardant packages. Also, Korean Patent No. KR 2010038701 discloses a flame retardant package useful in copolyetherester, which comprises an organic phosphinate metal salt, a melamine cyanurate, and an aromatic phosphate. However, as demonstrated in the examples below, the present Applicant discovered that when such prior art flame retardant packages are used in copolyetherester compositions, the flame retardants tend to migrate to the surface over time and cause blooming. Thus, there is still a need to develop a flame-retardant copolyetherester composition that is blooming free.

SUMMARY

Provided herein is a flame-retardant copolyetherester composition comprising:
(a) at least one copolyetherester;
(b) 5-35 wt % of at least one halogen-free flame retardant;
(c) 0.1-20 wt % of at least one nitrogen-containing compound;
(d) 0.1-10 wt % of at least one aromatic phosphate; and
(e) 0.1-10 wt % of at least at least one novolac resin,
with the total wt % of all components of the copolyetherester composition totaling to 100 wt %,
wherein the at least one halogen-free flame retardant comprises at least one selected from the group consisting of phosphinates of the formula (I), disphosphinates of the formula (II), and combinations or polymers thereof

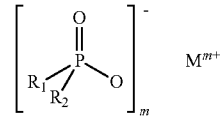

(I)

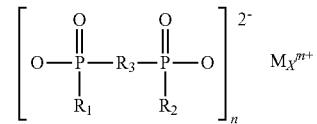

(II)

with $R_1$ and $R_2$ being identical or different and each of $R_1$ and $R_2$ being independently selected from hydrogen, a linear, branched, or cyclic $C_1$-$C_6$ alkyl group, or a $C_6$-$C_{10}$ aryl; $R_3$ being selected from a linear or branched $C_1$-$C_{10}$ alkylene group, a $C_6$-$C_{10}$ arylene group, a $C_6$-$C_{12}$ alkyl-arylene group, or a $C_6$-$C_{12}$ aryl-alkylene group; M being selected from calcium ions, aluminum ions, magnesium ions, zinc ions, antimony ions, tin ions, germanium ions, titanium ions, iron ions, zirconium ions, cerium ions, bismuth ions, strontium ions, manganese ions, lithium ions, sodium ions, potassium ions and combinations thereof; and m, n, and x each being a same or different integer of from 1-4, and
wherein the flame-retardant copolyetherester composition passes the UL1581 flammability standard.

In one embodiment of the flame-retardant copolyetherester composition, the at least one copolyetherester is present at a level of 15-94.7 wt %, or 40-94.7 wt %, or 40-90 wt %, with the total wt % of all components of the copolyetherester composition totaling to 100 wt %.

In a further embodiment of the flame-retardant copolyetherester composition, within the at least one halogen-free flame retardant, each of $R_1$ and $R_2$ is hydrogen, or the at least one halogen-free flame retardant is aluminum hypophosphite.

In a yet further embodiment of the flame-retardant copolyetherester composition, the at least one halogen-free flame retardant is present at a level of 5-30 wt % or 7.5-30 wt %, with the total wt % of all components of the copolyetherester composition totaling to 100 wt %.

In a yet further embodiment of the flame-retardant copolyetherester composition, the at least one nitrogen-containing compound is selected from the group consisting of (i) melamine cyanurate, (ii) condensation products of melamine, (iii) reaction products of phosphoric acid with melamine, and (iv) reaction products of phosphoric acid with condensation products of melamine, or the at least one nitrogen-containing compound is melamine cyanurate.

In a yet further embodiment of the flame-retardant copolyetherester composition, the at least one nitrogen-containing compound is present at a level of 1-15 wt % or 2-15 wt %, with the total wt % of all components of the copolyetherester composition totaling to 100 wt %.

In a yet further embodiment of the flame-retardant copolyetherester composition, the at least one aromatic phosphate is selected from the group consisting of trialkyl phosphates, triaryl phosphates, trialkylaryl phosphates, and combinations of two or more thereof, or the at least one aromatic phosphate is selected from the group consisting of triphenyl phosphate; tri(4-methylphenyl)phosphate; tri(2,6-dimethylphenyl)phosphate; tri(2,4,6-trimethylphenyl)phosphate; tri(2,4-ditertiary butylphenyl)phosphate; tri(2,6-ditertiary butylphenyl)phosphate; resorcinol bis(diphenyl phosphate) (RDP); bisphenol A bis(diphenyl phosphate) (BDP); resorcinol bis(dixylenyl phosphate) (XDP); hydroquinol bis(diphenyl phosphate); resorcinol bis-(di-2,6-dimethylphenyl phosphate); 4,4'-biphenyl bis-(di-2,6-dimethylphenyl phosphate); and combinations of two or more thereof.

In a yet further embodiment of the flame-retardant copolyetherester composition, the at least one novolac resin has a structure of the formula (IV):

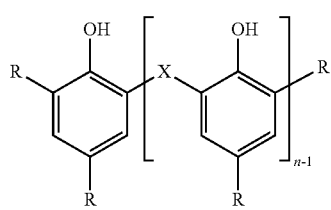

with X being $CH_2$, $CH_2CH_2$, $CHCH_3$, CO, or $SO_2$; each of R being independently or simultaneously a hydrogen atom, a halogen atom, a $C_{1-20}$ alkyl group, an aryl group, $NO_2$, CN, Si, or a hydroxyl group; and n being an integer of 1 or more.

In a yet further embodiment of the flame-retardant copolyetherester composition, the at least one novolac resin is present at a level of 0.1-7.5 wt % or 0.1-5 wt %, with the total wt % of all components of the copolyetherester composition totaling to 100 wt %.

Further provided herein is an article comprising at least one component part formed of the flame-retardant copolyetherester composition described above, preferably the article is selected from motorized vehicle parts and electrical/electronic devices. In one embodiment, the article is selected from insulated wires and cables, and preferably, the insulated wires and cables comprise one or more insulating layers and/or insulating jackets that are formed of the flame-retardant copolyetherester composition described above.

In accordance with the present disclosure, when a range is given with two particular end points, it is understood that the range includes any value that is within the two particular end points and any value that is equal to or about equal to any of the two end points.

DETAILED DESCRIPTION

Disclosed herein is a flame-retardant copolyetherester composition comprising,
(a) at least one copolyetherester;
(b) about 5-35 wt % of at least one halogen-free flame retardant;
(c) about 0.1-20 wt % of at least one nitrogen-containing compound
(d) about 0.1-10 wt % of at least one aromatic phosphate; and;
(e) about 0.1-10 wt % of at least one novolac resin.

The copolyetheresters suitable for use in the compositions disclosed herein may be copolymers having a multiplicity of recurring long-chain ester units and recurring short-chain ester units joined head-to-tail through ester linkages, the long-chain ester units being represented by formula (I):

and the short-chain ester units being represented by formula (II):

wherein,
G is a divalent radical remaining after the removal of terminal hydroxyl groups from poly(alkylene oxide) glycols having a number average molecular weight of about 400-6000;
R is a divalent radical remaining after the removal of carboxyl groups from a dicarboxylic acid having a number average molecular weight of about 300 or less;
D is a divalent radical remaining after the removal of hydroxyl groups from a glycol having a number average molecular weight of about 250 or less, and
wherein,
the at least one copolyetherester contains about 1-85 wt % of the recurring long-chain ester units and about 15-99 wt % of the recurring short-chain ester units.

In one embodiment, the copolyetherester used in the composition disclosed herein contains about 5-80 wt % of the recurring long-chain ester units and about 20-95 wt % of the recurring short-chain ester units.

In a further embodiment, the copolyetherester used in the composition disclosed herein contains about 10-75 wt % of the recurring long-chain ester units and about 25-90 wt % of the recurring short-chain ester units.

In a yet further embodiment, the copolyetherester used in the composition disclosed herein contains about 40-75 wt % of the recurring long-chain ester units and about 25-60 wt % of the recurring short-chain ester units.

As used herein, the term "long-chain ester units" refers to reaction products of a long-chain glycol with a dicarboxylic acid. Suitable long-chain glycols are poly(alkylene oxide)

glycols having terminal hydroxyl groups and a number average molecular weight of about 400-6000, or about 600-3000, which include, without limitation, poly(tetramethylene oxide) glycol, poly(trimethylene oxide) glycol, poly(propylene oxide) glycol, poly(ethylene oxide) glycol, copolymer glycols of these alkylene oxides, and block copolymers such as ethylene oxide-capped poly(propylene oxide) glycol. The long-chain glycols used herein may also be combinations of two or more of the above glycols. In one embodiment, the poly(alkylene oxide) glycols used herein are poly(tetramethylene oxide) glycols.

As used herein, the term "short-chain ester units" refers to reaction products of a low molecular weight glycol or an ester-forming derivative thereof with a dicarboxylic acid. Suitable low molecular weight glycols are those having a number average molecular weight of about 250 or lower, or about 10-250, or about 20-150, or about 50-100, which include, without limitation, aliphatic dihydroxy compounds, alicyclic dihydroxy compounds, and aromatic dihydroxy compounds (including bisphenols). In one embodiment, the low molecular weight glycol used herein is a dihydroxy compound having 2-15 carbon atoms, such as ethylene glycol; propylene glycol; isobutylene glycol; 1,4-tetramethylene glycol; pentamethylene glycol; 2,2-dimethyltrimethylene glycol; hexamethylene glycol; decamethylene glycol; dihydroxycyclohexane; cyclohexanedimethanol; resorcinol; hydroquinone; 1,5-dihydroxynaphthalene; or the like. In a further embodiment, the low molecular weight glycol used herein is a dihydroxy compound having 2-8 carbon atoms. In a yet further embodiment, the low molecular weight glycol used herein is 1,4-tetramethylene glycol. Bisphenols that are useful herein include, without limitation, bis(p-hydroxy)diphenyl, bis(p-hydroxyphenyl)methane, bis(p-hydroxyphenyl)propane, and mixtures of two or more thereof.

The ester-forming derivatives of low molecular weight glycols useful herein include those derived from the low molecular weight glycols described above, such as ester-forming derivatives of ethylene glycol (e.g., ethylene oxide or ethylene carbonate) or ester-forming derivatives of resorcinol (e.g., resorcinol diacetate). As used herein, the number average molecular weight limitations pertain to the low molecular weight glycols only. Therefore, a compound that is an ester-forming derivative of a glycol and has a number average molecular weight more than 250 can also be used herein, provided that the corresponding glycol has a number average molecular weight of about 250 or lower.

The "dicarboxylic acids" useful for reaction with the above described long-chain glycols or low molecular weight glycols are those low molecular weight (i.e., number average molecular weight of about 300 or lower, or about 10-300, or about 30-200, or about 50-100) aliphatic, alicyclic, or aromatic dicarboxylic acids.

The term "aliphatic dicarboxylic acids" used herein refers to those carboxylic acids having two carboxyl groups each attached to a saturated carbon atom. If the carbon atom to which the carboxyl group is attached to is saturated and is in an aliphatic ring, the acid is referred to as an "alicyclic dicarboxylic acid". The term "aromatic dicarboxylic acids" used herein refers to those dicarboxylic acids having two carboxyl groups each attached to a carbon atom in an aromatic ring structure. It is not necessary that both functional carboxyl groups in the aromatic dicarboxylic acid be attached to the same aromatic ring. Where more than one aromatic ring are present, they can be joined by aliphatic or aromatic divalent radicals or divalent radical such as —O— or —SO$_2$—.

The aliphatic or alicyclic dicarboxylic acids useful herein include, without limitation, sebacic acid; 1,3-cyclohexane dicarboxylic acid; 1,4-cyclohexane dicarboxylic acid; adipic acid; glutaric acid; 4-cyclohexane-1,2-dicarboxylic acid; 2-ethyl suberic acid; cyclopentane dicarboxylic acid; decahydro-1,5-naphthylene dicarboxylic acid; 4,4'-bicyclohexyl dicarboxylic acid; decahydro-2,6-naphthylene dicarboxylic acid; 4,4'-methylenebis(cyclohexyl) carboxylic acid; 3,4-furan dicarboxylic acid; and combinations of two or more thereof. In one embodiment, the dicarboxylic acids used herein are selected from cyclohexane dicarboxylic acids, adipic acids, and combinations of two or more thereof.

The aromatic dicarboxylic acids useful herein include, without limitation, phthalic acids; terephthalic acids; isophthalic acids; dibenzoic acids; dicarboxylic compounds with two benzene nuclei (such as bis(p-carboxyphenyl)methane; p-oxy-1,5-naphthalene dicarboxylic acid; 2,6-naphthalene dicarboxylic acid; 2,7-naphthalene dicarboxylic acid; or 4,4'-sulfonyl dibenzoic acid); and C$_1$-C$_{12}$ alkyl and ring substitution derivatives of the aromatic dicarboxylic acids described above (such as halo, alkoxy, and aryl derivatives thereof). The aromatic dicarboxylic acids useful herein may also be, for example, hydroxyl acids such as p-(β-hydroxyethoxy)benzoic acid.

In one embodiment of the compositions disclosed herein, the dicarboxylic acids used to form the copolyetheresters component may be selected from aromatic dicarboxylic acids. In a further embodiment, the dicarboxylic acids may be selected from aromatic dicarboxylic acids having about 8-16 carbon atoms. In a yet further embodiment, the dicarboxylic acids may be terephthalic acid alone or a combination of terephthalic acid with phthalic acid and/or isophthalic acid.

In addition, the dicarboxylic acids useful herein may also include functional equivalents of dicarboxylic acids. In forming the copolyetheresters, the functional equivalents of dicarboxylic acids reacts with the above described long-chain and low molecular weight glycols substantially the same way as dicarboxylic acids. Useful functional equivalents of dicarboxylic acids include ester and ester-forming derivatives of dicarboxylic acids, such as acid halides and anhydrides. As used herein, the number average molecular weight limitations pertain only to the corresponding dicarboxylic acids, not the functional equivalents thereof (such as the ester or ester-forming derivatives thereof). Therefore, a compound that is a functional equivalent of a dicarboxylic acid and has a number average molecular weight more than 300 can also be used herein, provided that the corresponding dicarboxylic acid has a number average molecular weight of about 300 or lower. Moreover, the dicarboxylic acids may also contain any substituent groups or combinations thereof that do not substantially interfere with the copolyetherester formation and the use of the copolyetherester in the compositions disclosed herein.

The long-chain glycols used in forming the copolyetherester component of the composition disclosed herein may also be mixtures of two or more long-chain glycols. Similarly, the low molecular weight glycols and dicarboxylic acids used in forming the copolyetherester component may also be mixtures of two or more low molecular weight glycols and mixtures of two or more dicarboxylic acids, respectively. In a preferred embodiment, at least about 70 mol % of the groups represented by R in Formulas (I) and (II) above are 1,4-phenolene radicals, and at least 70 mol % of the groups represented by D in Formula (II) above are 1,4-butylene radicals. When two or more dicarboxylic acids are used in forming the copolyetherester, it is preferred to use a mixture of terephthalic acid and isophthalic acid, while when two or more low molecular weight glycols are used, it is preferred to use a mixture of 1,4-tetramethylene glycol and hexamethylene glycol.

The at least one copolyetherester comprised in the flame-retardant copolyetherester composition disclosed herein may also be a blend of two or more copolyetheresters. It is not required that the copolyetheresters comprised in the blend, individually meet the weight percentages requirements disclosed hereinbefore for the short-chain and long-chain ester units. However, the blend of two or more copolyetheresters must conform to the values described hereinbefore for the copolyetheresters on a weighted average basis. For example, in a blend that contains equal amounts of two copolyetheresters, one copolyetherester may contain about 10 wt % of the short-chain ester units and the other copolyetherester may contain about 80 wt % of the short-chain ester units for a weighted average of about 45 wt % of the short-chain ester units in the blend.

In one embodiment, the at least one copolyetherester component comprised in the flame-retardant copolyetherester composition disclosed herein is obtained by the copolymerization of a dicarboxylic acid ester selected from esters of terephthalic acid, esters of isophthalic acid, and mixtures thereof, with a lower molecular weight glycol that is 1,4-tetramethylene glycol and a long-chain glycol that is poly(tetramethylene ether)glycol or ethylene oxide-capped polypropylene oxide glycol. In a further embodiment, the at least one copolyetherester is obtained by the copolymerization of an ester of terephthalic acid (e.g., dimethylterephthalate) with 1,4-tetramethylene glycol and poly(tetramethylene ether)glycol.

The copolyetheresters useful in the compositions disclosed herein may be made by any suitable methods known to those skilled in the art, such as by using a conventional ester interchange reaction.

In one embodiment, the method involves heating an dicarboxylic acid ester (e.g., dimethylterephthalate) with a poly(alkylene oxide)glycol and a molar excess of a low molecular weight glycol (e.g., 1,4-tetramethylene glycol) in the presence of a catalyst, followed by distilling off methanol formed by the interchange reaction and continuing the heat until methanol evolution is complete. Depending on the selection of temperatures and catalyst types and the amount of the low molecular weight glycols used, the polymerization may be completed within a few minutes to a few hours and results in formation of a low molecular weight pre-polymer. Such pre-polymers can also be prepared by a number of alternate esterification or ester interchange processes, for example, by reacting a long-chain glycol with a short-chain ester homopolymer or copolymer in the presence of catalyst until randomization occurs. The short-chain ester homopolymer or copolymer can be prepared by the ester interchange either between a dimethyl ester (e.g., dimethylterephthalate) and a low molecular weight glycol (e.g, 1,4-tetramethylene glycol) as described above, or between a free acid (e.g., terephthalic acid) and a glycol acetate (e.g., 1,4-butanediol diacetate). Alternatively, the short-chain ester homopolymer or copolymer can be prepared by direct esterification from appropriate acids (e.g., terephthalic acid), anhydrides (e.g., phthalic anhydride), or acid chlorides (e.g., terephthaloyl chloride) with glycols (e.g., 1,4-tetramethylene glycol). Or, the short-chain ester homopolymer or copolymer may be prepared by any other suitable processes, such as the reaction of dicarboxylic acids with cyclic ethers or carbonates.

Further, the pre-polymers obtained as described above can be converted to high molecular weight copolyetheresters by the distillation of the excess low molecular weight glycols. Such process is known as "polycondensation". Additional ester interchange occurs during the polycondensation process to increase the molecular weight and to randomize the arrangement of the copolyetherester units. In general, to obtained the best results, the polycondensation may be run at a pressure of less than about 1 mmHg and a temperature of about 240-260° C., in the presence of antioxidants (such as 1,6-bis-(3,5-di-tert-butyl-4-hydroxyphenol)propionamido]-hexane or 1,3,5-trimethyl-2,4,6-tris[3,5-di-tert-butyl-4-hydroxybenzyl]benzene), and for less than about 2 hours. In order to avoid excessive holding time at high temperatures with possible irreversible thermal degradation, it is advantageous to employ a catalyst for ester interchange reactions. A wide variety of catalysts can be used herein, which include, without limitation, organic titanates (such as tetrabutyl titanate alone or in combination with magnesium or calcium acetates), complex titanates (such as those derived from alkali or alkaline earth metal alkoxides and titanate esters), inorganic titanates (such as lanthanum titanate), calcium acetate/antimony trioxide mixtures, lithium and magnesium alkoxides, stannous catalysts, and mixtures of two or more thereof.

The copolyetheresters useful in the compositions disclosed herein can also be obtained commercially from E.I. du Pont de Nemours and Company (U.S.A.) (hereafter "DuPont") under the trade name Hytrel®.

Based on the total weight of the flame-retardant copolyetherester composition disclosed herein, the at least one copolyetherester may be present at a concentration of about 25-94.7 wt %, or about 40-94.7 wt %, or about 40-90 wt %.

Halogen-free flame retardants suitable for use in the compositions disclosed herein may be selected from phosphinates of the formula (I), disphosphinates of the formula (II), and combinations or polymers thereof

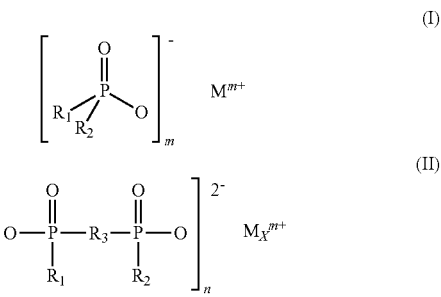

wherein $R_1$ and $R_2$ may be identical or different and each of $R_1$ and $R_2$ is independently selected from hydrogen, a linear, branched, or cyclic $C_1$-$C_6$ alkyl group, or a $C_6$-$C_{10}$ aryl group; $R_3$ is a linear or branched $C_1$-$C_{10}$ alkylene group, a $C_6$-$C_{10}$ arylene group, a $C_6$-$C_{12}$ alkyl-arylene group, or a $C_6$-$C_{12}$ aryl-alkylene group; M is selected from calcium ions, aluminum ions, magnesium ions, zinc ions, antimony ions, tin ions, germanium ions, titanium ions, iron ions, zirconium ions, cerium ions, bismuth ions, strontium ions, manganese ions, lithium ions, sodium ions, potassium ions and combinations thereof; each of m, n, and x is the same or different integer from 1 to 4. Preferably, $R_1$ and $R_2$ may be independently selected from hydrogen, methyl, ethyl, n-propyl, isopropyl, n-butyl, tert-butyl, n-pentyl, and phenyl; $R_3$ may be selected from methylene, ethylene, n-propylene, isopropylene, n-butylene, tert-butylene, n-pentylene, n-octylene, n-dodecylene, phenylene, naphthylene, methylphenylene, ethylphenylene, tert-butylphenylene, methylnaphthylene, ethylnaphthylene, tert-butylnaphthylene, phenylmethylene, phenylethylene, phenylpropylene, and phenylbutylene; and M may be selected from aluminum and zinc ions. More preferably, the phosphinates used here may be selected from aluminum methylethylphosphinate, aluminum diethylphosphinate, and combinations thereof.

An example of the halogen-free flame retardants useful herein may be obtained commercially from Clariant (Switzerland) under the trade name Exolit™ OP.

In a yet further embodiment, the halogen-free flame retardant used herein is a aluminum hypophosphite, which may be obtained commercially from Italmatch Chemicals (Italy) under the trade name Phoslite™ IP-A.

Based on the total weight of the flame-retardant copolyetherester composition disclosed herein, the at least one halogen-free flame retardant may be present at a concentration of about 5-35 wt %, or about 5-30 wt %, or about 7.5-30 wt %.

The nitrogen containing compounds used herein may include, without limitation, those described, for example in U.S. Pat. Nos. 6,365,071; and 7,255,814.

In one embodiment, the nitrogen containing compounds used herein are selected from melamine, benzoguanamine, tris(hydroxyethyl)isocyanurate, allantoine, glycouril, dicyandiamide, guanidine, carbodiimide, and derivatives thereof.

In a further embodiment, the nitrogen containing compounds used herein may be selected from melamine derivatives, which include, without limitation, (i) melamine cyanurate, (ii) condensation products of melamine, (iii) reaction products of phosphoric acid with melamine, and (iv) reaction products of phosphoric acid with condensation products of melamine. Suitable condensation products may include, without limitation, melem, melam, melon, as well as higher derivatives and mixtures thereof. Condensation products of melamine can be produced by any suitable methods (e.g., those described in PCT Patent Publication No. WO9616948). Reaction products of phosphoric acid with melamine or reaction products of phosphoric acid with condensation products of melamine are herein understood compounds, which result from the reaction of melamine with a phosphoric acid or the reaction of a condensation product of melamine (e.g., melem, melam, or melon) with a phosphoric acid. Examples include, without limitation, dimelaminephosphate, dimelamine pyrophosphate, melamine phosphate, melamine polyphosphate, melamine pyrophosphate, melamine polyphosphate, melam polyphosphate, melon polyphosphate, and melem polyphosphate, as are described, e.g., in PCT Patent Publication No. WO9839306.

In a yet further embodiment, the at least one nitrogen containing compound used herein is selected from melamine phosphate and melamine cyanurate. In a yet further embodiment, the at least one nitrogen containing compound used herein is melamine cyanurate.

Based on the total weight of the flame-retardant copolyetherester composition disclosed herein, the at least one nitrogen containing compound may be present at a concentration of about 0.1-20 wt %, or about 1-15 wt %, or about 2-15 wt %.

The aromatic phosphate used herein may be represented by the following general formula (III):

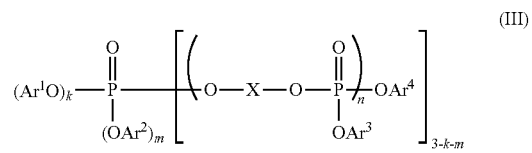

In formula (III), n indicates an integer of 0 or more, and the compound may be a mixture with different integers of n. k and m each indicates an integer of 0 to 2, and (k+m) is an integer of 0 to 2. Preferably, k and m each is an integer of 0 or 1; more preferably, k and m are both 1. $Ar^1$, $Ar^2$, $Ar^3$, and $Ar^4$ in formula (III) are the same or different, and each represents a phenyl group, or a phenyl group substituted by an organic residue containing no halogen. Their specific examples include, without limitation, a phenyl group, a tolyl group, a xylyl group, a cumenyl group, a mesityl group, a naphthyl group, an indenyl group, an anthryl group, etc. Preferred are a phenyl group, a tolyl group, a xylyl group, a cumenyl group, and a naphthyl group; and more preferred are a phenyl group, a tolyl group, and a xylyl group. Finally, X in formula (III) represents any of the following:

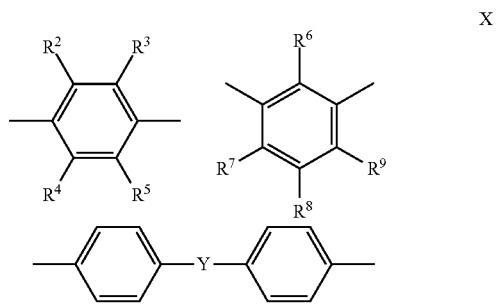

In these, $R^2$ to $R^9$ are the same or different, and each represents a hydrogen atom, or an alkyl group having from 1 to 5 carbon atoms. Specific examples of the alkyl group having from 1 to 5 carbon atoms are a methyl group, an ethyl group, an n-propyl group, an isopropyl group, an n-butyl group, a sec-butyl group, a tert-butyl group, etc. For these, preferred are a hydrogen atom, a methyl group, and an ethyl group; and more preferred is a hydrogen atom. Y represents a direct bond, O, S, $SO_2$, $C(CH_3)_2$, $CH_2$, or CHPh, with Ph representing a phenyl group.

Exemplary aromatic phosphates used herein include, without limitation, triaryl phosphates (e.g., triphenyl phosphate, tricresyl phosphate, trixylenyl phosphate, cresyl diphenyl phosphate) and trialkylaryl phosphates (e.g., octyldiphenyl phosphate). Preferably, the aromatic phosphates used herein are selected from triphenyl phosphate; tri(4-methylphenyl) phosphate; tri(2,6-dimethylphenyl)phosphate; tri(2,4,6-trimethylphenyl)phosphate; tri(2,4-ditertiary butylphenyl)phosphate; tri(2,6-ditertiary butylphenyl)phosphate; resorcinol bis(diphenyl phosphate) (RDP); bisphenol A bis(diphenyl phosphate) (BDP); resorcinol bis(dixylenyl phosphate) (XDP); hydroquinol bis(diphenyl phosphate); resorcinol bis-(di-2,6-dimethylphenyl phosphate); 4,4'-biphenyl bis-(di-2,6-dimethylphenyl phosphate); and the like.

The aromatic phosphates used herein may also be obtained commercially from Daihachi Chemical Industry Co., Ltd. (Japan) under the trade name PX-200 (resorcinol bis-(di-2,6-dimethylphenyl phosphate), CAS Number: 139189-30-3) or PX-202 (4,4'-biphenyl bis-(di-2,6-dimethylphenyl phosphate), CAS Number: 147263-99-8).

Based on the total weight of the flame-retardant copolyetherester composition disclosed herein, the at least one aromatic phosphate may be present at a concentration of about 0.1-10 wt %, or about 0.1-7.5 wt %, or about 0.1-5 wt %.

The novolac resins used herein are obtained by reacting phenols and formaldehyde in the presence of an acidic catalyst and may have a structure of the following formula (IV)

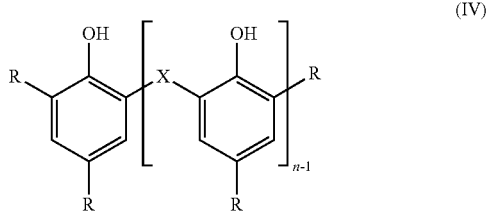

(IV)

Within formula (IV), X is selected from $CH_2$, $CH_2CH_2$, $CHCH_3$, CO, or $SO_2$; each of R is independently or simultaneously a hydrogen atom, a halogen atom, a $C_{1-20}$ alkyl group, an aryl group, $NO_2$, CN, Si, or a hydroxyl group; and n is an integer of 1 or more, showing degree of polymerization.

Examples of the novolac resins used herein may also be obtained commercially from SI Group (U.S.A.) under the trade name ReziCure™ 3025, ReziCure™ 3057, T-4000, or T-5000.

Based on the total weight of the flame-retardant copolyetherester composition disclosed herein, the at least one novolac resin may be present at a concentration of about 0.1-10 wt %, or about 0.1-7.5 wt %, or about 0.1-5 wt %.

The flame-retardant copolyetherester composition disclosed herein may further comprise other additives, such as colorants, antioxidants, UV stabilizers, UV absorbers, heat stabilizers, lubricants, tougheners, impact modifiers, reinforcing agents, viscosity modifiers, nucleating agents, plasticizers, mold release agents, scratch and mar modifiers, impact modifiers, emulsifiers, pigments, optical brighteners, antistatic agents, fillers, and combinations of two or more thereof. Suitable fillers may be selected from calcium carbonates, silicates, talcum, carbon black, and combinations of two or more thereof. Based on the total weigh of the composition disclosed herein, such additional additive(s) may be present at a concentration of about 0.01-20 wt % or about 0.01-10 wt %, or about 0.2-5 wt %, or about 0.5-2 wt %.

The copolyetherester compositions disclosed herein are melt-mixed blends, wherein all of the polymeric components are well-dispersed within each other and all of the non-polymeric ingredients are homogeneously dispersed in and bound by the polymer matrix, such that the blend forms a unified whole. Any melt-mixing method may be used to combine the polymeric components and non-polymeric ingredients of the composition disclosed herein.

As discussed in the background section, when non-halogen flame additives are used in copolyetherester compositions, the flame retardant additives often migrate to the surface of the final product. PCT Patent Application No. WO 2011/120225 teaches that in thermoplastic polyurethane elastomers, the addition of solid phosphates (such as XDP or resorcinol bis-(di-2,6-dimethylphenyl phosphate)) instead of liquid phosphates (such as BDP or RDP) may solve the blooming issue. However, as demonstrated by the examples presented below, in copolyetheresters, even the addition of resorcinol bis-(di-2,6-dimethylphenyl phosphate) fails to prevent blooming. While it is found that the addition of novolac resins could solve the blooming issue.

Blooming of the flame-retardant copolyetherester compositions described herein is determined by a visual inspection of molded plaques prepared from the flame-retardant copolyetherester compositions using the human eye without any magnification. If any deposits of powder-like or liquid like material were visible upon inspection of the surface of the molded plaque, then the molded plaque was considered to exhibit blooming. If there were no visible deposits of powder-like or liquid like material on the surface of the molded plaque, then the molded plaque was considered to exhibit no blooming.

Flammability of the flame-retardant copolyetherester compositions disclosed herein was determined using UL1581 test standard for flammability. Samples tested using this method either passed the flammability test or failed the flammability test with the flammability results listed in Table 1 under VW-1 as pass or fail.

Further disclosed herein are articles comprising one or more component parts formed of the flame-retardant copolyetherester compositions disclosed herein, wherein the articles include, without limitation, motorized vehicles, electrical/electronic devices, furniture, footwear, roof structure, outdoor apparels, water management system, etc.

In one embodiment, the articles are selected from motorized vehicles. In such embodiments, the flame-retardant copolyetherester compositions disclosed herein may be used to form component parts such as airduct, constant velocity joint (CVJ) boot, etc.

In a further embodiment, the articles are selected from electrical/electronic devices. In such embodiments, the flame-retardant copolyetherester composition disclosed herein may be used to form insulating layers or jacket for wire and cable. More particularly, the articles may be selected from wires and cables, which comprise insulating layers and/or jackets formed of the flame-retardant copolyetherester compositions disclosed herein. For example, the article may be an insulated wire or cable, which comprises two or three electrically conductive cores, two or three insulating layers each surrounding one of the electrically conductive cores, and optionally a insulating jacket surrounding the electrically conductive cores and the insulating layers, wherein the insulating layers and/or the insulating jacket are formed of the flame-retardant copolyetherester composition disclosed herein.

EXAMPLES

Material

Copolyetherester: copolyetherester elastomer obtained from DuPont under the trade name Hytrel® 3078;
AO-1: antioxidant concentrate obtained from DuPont under the trade name Hytrel® 30HS;
AO-2: hindered phenolic antioxidant obtained from BASF (Germany) under the trade name Irganox™ 1010;
AO-3: trisarylphosphite processing stabilizer obtained from BASF under the trade name Irgafos™ 168;
FR: a flame retardant masterbatch comprising 60 wt % of aluminum hypophosphite (obtained from Italmatch under the trade name Phoslite™ IP-A) and 40 wt % of copolyetherester (obtained from DuPont under the trade name Hytrel® 3078);

MC: melamine cyanurate obtained from Hangzhou JLS Flame Retardants Chemical Co., Ltd. (China) under the trade name JLS-MC15

Aromatic Phosphate: resorcinol bis-(di-2,6-dimethylphenyl) phosphate obtained from Daihachi Chemical Industry Co., Ltd. (Japan) under the trade name PX-200;

Novolac-1: thermoplastic phenolic resin obtained from SI group under the trade name ReziCure™ 3025;

Novolac-2: thermoplastic phenolic resin obtained from SI group under the trade name T-4000.

Comparative Example CE1 and Examples E1-E2

In each of the Comparative Example and Examples, a copolyetherester composition resin was prepared as follows: appropriate amounts of copolyetherester, flame retardants, and other additives were dried, pre-mixed, and melt blended in a ZSK26 twin-screw extruder (purchased from Coperion Werner & Pfleiderer GmbH & Co., Germany) with the extruder temperature set at 190-210° C., the extrusion speed at 300 rpm, and the throughput at 20 kg/hr.

In each example, insulated conducting wires were prepared using the resins obtained above, wherein each of the insulated conducting wires had a circular cross section and a diameter of about 2 mm, and wherein each of the insulated conducting wires had an insulating jacket made of the copolyetherester composition and encircling conductive core that was made of 91 stranded copper wires. Following UL1581, the flammability (VW-1), tensile-strength, and ultimate-elongation of the insulated conducting wires as such prepared were measured and results are tabulated in Table 1 below.

In each example, 100×100×2 mm molding plaques were prepared by injection molding with the temperature of the molding machine set at 190-210° C. and the temperature of the mold at 50° C. Then the hardness of the molding plaques were measured in accordance to ISO868 and the results are tabulated in Table 1.

Finally, the molding plaques in each example were conditioned in a climate controlled chamber that was set at 65° C. and 95% relative humidity (RH) for 3 days. Thereafter, the conditioned molding plaques were inspected visually for blooming.

The results demonstrate that when non-halogen flame additives are used in copolyetherester compositions, the flame retardant additives often migrate to the surface of the final product. However, it is found that the addition of novolac resins could solve the blooming issue. In addition, when the copolyetherester composition is used to form an insulating jacket, the VW-1 flammability rating (in accordance to UL1581) thereof is also improved with the addition of novolac resins.

TABLE 1

|  | CE1 | E1 | E2 |
| --- | --- | --- | --- |
| Copolyetherester | 39.33 | 42.93 | 42.93 |
| AO-1 | 4 | — | — |
| AO-2 | — | 0.2 | 0.2 |
| AO-3 | — | 0.2 | 0.2 |
| FR | 41.67 | 41.67 | 41.67 |
| MC | 10 | 10 | 10 |
| Aromatic Phosphate | 5 | 2.5 | 2.5 |
| Novolac-1 | — | 2.5 | — |
| Novolac-2 | — | — | 2.5 |
| Properties | | | |
| Hardness Shore A, 15 s | 88.5 | 88.5 | 87.9 |
| Tensile-Strength (MPa) | 9.68 | 12.73 | 10.48 |

TABLE 1-continued

|  | CE1 | E1 | E2 |
| --- | --- | --- | --- |
| Ultimate-Elongation (%) | 770.18 | 829.77 | 738.27 |
| VW-1 | Fail | Pass | Pass |
| Blooming | [1]Y | [2]N | [2]N |

[1]Y: Deposits of powder-like or liquid like material was observed;
[2]N: No deposit of powder-like or liquid like material was observed.

What is claimed is:

1. A flame-retardant copolyetherester composition comprising:
   (a) at least one copolyetherester;
   (b) 5-35 wt % of at least one halogen-free flame retardant;
   (c) 0.1-20 wt % of at least one nitrogen-containing compound;
   (d) 0.1-10 wt % of at least one aromatic phosphate; and
   (e) 0.1-10 wt % of at least one novolac resin,
with the total wt % of all components of the copolyetherester composition totaling to 100 wt %,
wherein the flame-retardant copolyetherester composition passes the UL1581 flammability standard, and
wherein the at least one halogen-free flame retardant is selected from the group consisting of phosphinates of the formula (I), disphosphinates of the formula (II), and combinations or polymers thereof

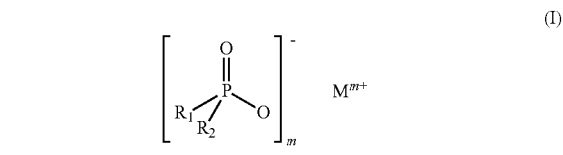

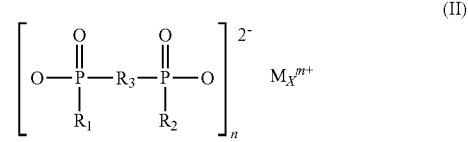

with $R_1$ and $R_2$ being identical or different and each of $R_1$ and $R_2$ is independently selected from hydrogen, a linear, branched, or cyclic $C_1$-$C_6$ alkyl group, or a $C_6$-$C_{10}$ aryl; $R_3$ being selected from a linear or branched $C_1$-$C_{10}$ alkylene group, a $C_6$-$C_{10}$ arylene group, a $C_6$-$C_{12}$ alkyl-arylene group, or a $C_6$-$C_{12}$ aryl-alkylene group; M being selected from the group consisting of calcium ions, aluminum ions, magnesium ions, zinc ions, antimony ions, tin ions, germanium ions, titanium ions, iron ions, zirconium ions, cerium ions, bismuth ions, strontium ions, manganese ions, lithium ions, sodium ions, potassium ions and combinations thereof; and m, n, and x each being the same or different integer from 1 to 4.

2. The flame-retardant copolyetherester composition of claim 1, wherein the at least one copolyetherester is present at a concentration of 25-94.7 wt %, with the total wt % of all components of the copolyetherester composition totaling to 100 wt %.

3. The flame-retardant copolyetherester composition of claim 1, wherein the at least one copolyetherester is present at a concentration of 40-94.7 wt %, with the total wt % of all components of the copolyetherester composition totaling to 100 wt %.

4. The flame-retardant copolyetherester composition of claim 1, wherein the at least one copolyetherester is present at a concentration of 40-90 wt %, with the total wt % of all components of the copolyetherester composition totaling to 100 wt %.

5. The flame-retardant copolyetherester composition of claim 1, wherein in the at least one halogen-free flame retardant, each of $R_1$ and $R_2$ is hydrogen.

6. The flame-retardant copolyetherester composition of claim 1, wherein the at least one halogen-free flame retardant is aluminum hypophosphite.

7. The flame-retardant copolyetherester composition of claim 1, wherein the at least one halogen-free flame retardant is present at a concentration of 5-30 wt %, with the total wt % of all components of the copolyetherester composition totaling to 100 wt %.

8. The flame-retardant copolyetherester composition of claim 1, wherein the at least one halogen-free flame retardant is present at a concentration of 7.5-30 wt %, with the total wt % of all components of the copolyetherester composition totaling to 100 wt %.

9. The flame-retardant copolyetherester composition of claim 1, wherein the at least one nitrogen-containing compound is selected from the group consisting of (i) melamine cyanurate, (ii) condensation products of melamine, (iii) reaction products of phosphoric acid with melamine, and (iv) reaction products of phosphoric acid with condensation products of melamine, or wherein, the at least one nitrogen-containing compound is melamine cyanurate.

10. The flame-retardant copolyetherester composition of claim 1, wherein the at least one nitrogen-containing compound is melamine cyanurate.

11. The flame-retardant copolyetherester composition of claim 1, wherein the at least one nitrogen-containing compound is present at a concentration of 1-15 wt %, with the total wt % of all components of the copolyetherester composition totaling to 100 wt %.

12. The flame-retardant copolyetherester composition of claim 1, wherein the at least one nitrogen-containing compound is present at a concentration of 2-15 wt %, with the total wt % of all components of the copolyetherester composition totaling to 100 wt %.

13. The flame-retardant copolyetherester composition of claim 1, wherein the at least one aromatic phosphate is selected from the group consisting of trialkyl phosphates, triaryl phosphates, trialkylaryl phosphates, and combinations of two or more thereof.

14. The flame-retardant copolyetherester composition of claim 1, wherein the at least one aromatic phosphate is selected from the group consisting of triphenyl phosphate; tri(4-methylphenyl)phosphate; tri(2,6-dimethylphenyl)phosphate; tri(2,4,6-trimethylphenyl)phosphate; tri(2,4-ditertiary butylphenyl)phosphate; tri(2,6-ditertiary butylphenyl)phosphate, resorcinol bis(diphenyl phosphate) (RDP); bisphenol A bis(diphenyl phosphate) (BDP); resorcinol bis(dixylenyl phosphate) (XDP); hydroquinol bis(diphenyl phosphate); resorcinol bis-(di-2,6-dimethylphenyl phosphate); 4,4'-biphenyl bis-(di-2,6-dimethylphenyl phosphate); and combinations of two or more thereof.

15. The flame-retardant copolyetherester composition of claim 1, wherein the at least one novolac resin has a structure of the formula (IV):

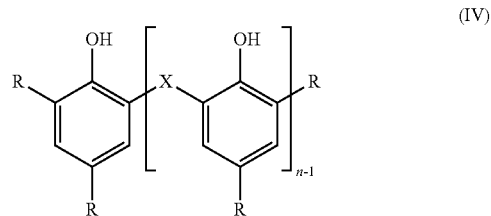

with X being selected from $CH_2$, $CH_2CH_2$, $CHCH_3$, CO, or $SO_2$; each R being independently or simultaneously selected from a hydrogen atom, a halogen atom, a $C_{1-20}$ alkyl group, an aryl group, $NO_2$, CN, Si, or a hydroxyl group; and n being an integer of 1 or more.

16. The flame-retardant copolyetherester composition of claim 1, wherein the at least one novolac resin is present at a concentration of 0.1-7.5 wt %, with the total wt % of all components of the copolyetherester composition totaling to 100 wt %.

17. The flame-retardant copolyetherester composition of claim 1, wherein the at least one novolac resin is present at a concentration of 0.1-5 wt %, with the total wt % of all components of the copolyetherester composition totaling to 100 wt %.

18. An article comprising at least one component part formed from the flame-retardant copolyetherester composition of claim 1.

19. The article of claim 18, wherein the article is a motorized vehicle part or electrical/electronic device.

20. The article of claim 18, wherein the article is selected from insulated wires and cables, said insulated wires and cables comprising one or more insulating layers or insulating jackets.

* * * * *